(12) United States Patent
Glenn et al.

(10) Patent No.: US 8,163,309 B2
(45) Date of Patent: Apr. 24, 2012

(54) STARCH FOAM MICROPARTICLES

(75) Inventors: Gregory M. Glenn, American Canyon, CA (US); Artur P. Klamczynski, Foster City, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 718 days.

(21) Appl. No.: 11/607,714

(22) Filed: Dec. 1, 2006

(65) Prior Publication Data

US 2008/0131538 A1 Jun. 5, 2008

(51) Int. Cl.
*A61K 36/00* (2006.01)

(52) U.S. Cl. ...................................................... 424/725

(58) Field of Classification Search ........................ None
See application file for complete search history.

(56) References Cited

U.S. PATENT DOCUMENTS

| | | | | |
|---|---|---|---|---|
| 5,648,095 A | | 7/1997 | Illum et al. | |
| 5,755,890 A | * | 5/1998 | Yuan | 127/71 |
| 5,958,589 A | | 9/1999 | Glenn et al. | |
| 5,998,485 A | * | 12/1999 | Tyan et al. | 514/724 |
| 6,325,859 B1 | * | 12/2001 | De Roos et al. | 131/276 |

OTHER PUBLICATIONS

Stoddard, F. L. Survey of Starch Particle-Size Distribution in Wheat and Related Species. Cereal Chem, vol. 76, No. 1 (1999) 145-149.*

Wikingsson et al. "Polyacryl starch microparticles as adjuvant in oral immunisation, inducing mucosal and systemic immune responses in mice". Vaccine, vol. 20, Issues 27-28 (Sep. 10, 2002) 3355-3363, abstract.*

Hayashi, H. "Properties of Food Powders." in: Encyclopedia of Agricultural, Food and Biological Engineering (2003), vol. 1, No. 1, pp. 808-810.*

Macedo, P. A., et al. "Using inert dusts to detect and assess varroa infestations in honey bee colonies". Journal of Apicultural Research, No. 40, vol. 1-2 (2002), pp. 3-7.*

Tan et al. "Effect of Oil Loading on Microspheres Produced by Spray Drying". Journal of Microencapsulation, No. 22, vol. 3 (May 2005) 253-259).*

Amarine et al. "Results of Research: Using Essential Oils for Honey Bee Mite Control". Internet Publication Date: Dec. 30, 1996 [retrieved from the Internet on: Nov. 11, 2010]. Retrieved from the Internet : <URL: http://www.wvu.edu/~agexten/varroa/varroa2.htm>.*

Glenn, G.M., and D.W. Irving, "Starch-Based Microcellular Foams," Carbohydrates (1995) 72(2):155-161.

Glenn, G.M., R.E. Miller, and D.W. Irving, "Microcellular Starch-Based Foams," In: ACS Agricultural Material as Renewable Resources (1996) Chapter 7 pp. 88-106.

Amrine, J., B. Noel, H. Mallow, T. Stasny, and R. Skidmore, "Results of Research: Using Essential Oils for Honey Bee Mite Control," (1996) http://www.wvu.edu/~agexten/ipm/insects/pollinat/varroa/varroa2.htm.

* cited by examiner

*Primary Examiner* — Amy L Clark (74) *Attorney, Agent, or Firm* — Elizabeth Sampson; Leslie Shaw; John Fado (57) ABSTRACT

The present invention relates to starch foam microparticles having a porous structure, and which typically have a diameter of less than or equal to about 50 microns. The present invention also relates to novel uses for the starch foam microparticles in beekeeping and in the pharmaceutical, plastics and fragrance industries.

25 Claims, 5 Drawing Sheets

STARCH FOAM MICROPARTICLES

FIELD OF THE INVENTION

The invention relates to starch foam microparticles having a porous structure and having a diameter at their widest point of less than or equal to about 50 microns (μm).

BACKGROUND OF THE INVENTION

Powders are a complex mixture of solid particles and/or granules interspersed with air. The powder form is often useful. For example, from an application perspective, powders are less labor intensive to handle and are easier and more accurately measured than are other forms of solid materials e.g., solid blocks. Free-flowing powders are easily mixed and blended and facilitate the handling and packaging of a product on the commercial scale.

As is well known in the art, starch, in its native form, is a free flowing powder. The native starch powder is comprised of solid particles of starch that are typically of a size that is between about 4 μm and 100 μm, and have an average density of about 1.4 g/cm$^3$. Starch is an abundant, useful, and inexpensive natural biodegradable material. In the form of a free-flowing powder, starch is easy to handle and package on a commercial scale. Free-flowing starch powders can also be easily mixed and blended with other powders.

Starch powders are potentially useful carrier agents. As noted above, starch is edible and biodegradable. Thus, because it is also abundant and inexpensive, it is ideal for applications that require a carrier agent to be edible and/or biodegradable. Unfortunately however, native starch powders have only a limited ability to function as carrier agents, particularly for liquid substances.

Indeed, only thin film of liquid can be formed around each individual starch granule when the native starch powder is mixed with a non-aqueous liquid e.g., an oil. Thus, only a small percentage of the oil can be loaded onto the starch powder before the flow properties begin to change. Loading more than about 5% oil (weight basis) onto native starch powder markedly affects the flowability and dispersion of the starch. In fact, loading more than 5% oil leads to agglomeration of the starch granules.

As noted above, native starch powder typically comprises particles that are in a size range from about 4 μm to about 100 μm. However, the range of potential applications for which starch is useful would be extended if smaller particle sizes were available. An exemplary application is in the plastics industry. Another exemplary application is in the beekeeping industry. Other exemplary applications are found, but not limited to the pharmaceutical industry and the fragrance industry.

Thus, there exists a need in the art for free flowing powders comprising small starch particles and for free flowing small starch particles loaded with substantial quantities of non-aqueous liquid. Fortunately, as will be clear from the following disclosure, the present invention provides for this and other needs.

SUMMARY OF THE INVENTION

In one embodiment, the present invention provides a starch foam microparticle that has a porous structure, and has a diameter of less than or equal to about 50 microns (μm) at it widest point. In an exemplary embodiment, starch foam microparticles are comprised of a plant starch that is a member selected from the group consisting of cereal starch and tuber starch or a combination of such members.

In one exemplary embodiment, the starch foam microparticle is saturated with a non-aqueous liquid.

In another exemplary embodiment the invention provides a method for controlling *Varroa* mites in bee colonies.

In another embodiment the invention provides a plastic film product comprising starch foam microparticles.

Other features, objects and advantages of the invention will be apparent from the detailed description which follows.

BRIEF DESCRIPTION OF THE DRAWINGS

FIG. 1. Scanning electron micrographs of corn starch under different processing conditions. (A)—Native starch granules that have not been heated in water (Scale bar=10 μm); (B) Native starch granules heated to about 90° C. for 1 minute. Note that the starch granules are swelling and leaking out some of the low molecular weight molecules (amylose). (Scale bar=5 μm). (C)—A starch sample that has been cooked at 95° C. for 30 minutes. The sample has been sliced in half. Notice the starch granule envelope and all of the fibrous starch has leaked out of the granules and formed a porous network. (Scale bar=5 um). (D)—Even after cooking the starch at 95° C. for 60 minutes, the starch granule envelope is still visible in the foam matrix (Scale bar=20 um). (E)—Starch sample cooked at 110° C. for about 15 minutes. Notice that the starch granule or envelope is almost completely dissolved. (Scale bar=10 μm). (F) Starch sample was cooked at 120° C. Notice there is little evidence of any remaining starch envelope. (Scale bar=3 μm). Thus, heat dissolves the starch granule remnant/envelope.

DETAILED DESCRIPTION OF THE INVENTION

Definitions

As used herein, the term "control" or "controlling" as in e.g., the phrase: the "control" of *Varroa* mites, or "controlling" *Varroa* mites, or as in the phrase: "controlling" agricultural pests, refers to any means for preventing infection or infestation, reducing the population of already infected areas or organisms, or elimination of the population of pests or mites or other species whose "control" is desired. Indeed, "controlling" as used herein refers to any indica of success in prevention, elimination, reduction or amelioration of a pest population or pest problem.

The term "starch" as used herein refers to a carbohydrate compound having the formula $(C_6H_{10}O_5)n$, where the subscript "n" denotes the total number of glucose monomer units. Typically, starches comprise the polysaccharides amylose and amylopectin. The amylose polysaccharide is comprised primarily of glucose monomer units joined to one another in α-1,4 linkages. Amylose is typically considered a linear molecule, however some minor branching sometimes is found. Typically, amylose polymers range in length from between about 500 to about 20,000 glucose monomer units, but any length is possible. Amylopectin is also comprised of glucose monomer units, but is not usually considered to be a strictly linear molecule. Instead, the polysaccharide comprises α-1,4 linked glucose monomers interspersed at intervals with branches formed by glucose monomers in α-1,6 linkage (see e.g., Advances in Food and Nutrition Research, Vol. 41: *Starch: Basic Science to Biotechnology*, Mirta Noemi Sivak and Jack Preiss eds. Academic Press (1998) which is incorporated herein by reference in its entirety).

The relative content of amylose and amylopectin in starch can vary. Typically, amylose comprises about 20% to about 25% to about 30% of the starch, but may be present in higher concentrations as well. For example "high-amylose corn starch" (HACS) comprises at least about 40% amylose, and in some embodiments comprises about 50%, about 55%, about 60%, about 65%, about 70%, about 75% amylose, and in other embodiments comprises about 80% amylose or about 85% amylose. Amylopectin on the other hand, typically comprises about 70% to about 75%, to about 80% of the starch, but may occur in higher proportions or lower proportions as well, e.g., waxy corn starch may comprise more than 99% amylopectin, and HACS may comprise as little as 15% amylopectin or less.

Starch is found in nearly every type of plant tissue including, but not limited to the fruit, seeds, stems, leaves, rhizomes and/or tubers. Thus, many starches are plant derived starches or "plant starch". Typically, starch produced in the USA is derived from corn, potatoes, rice, and wheat. However, useful starches can come from any source e.g., arrowroot, tapioca (cassava), buckwheat, banana, barley, cassava, konjac, kudzu, oca, sago, sorghum, sweet potato, taro, yams and beans e.g., favas, lentils and peas.

The term "starch" as used herein, also refers to "modified starch" which has been modified by human intervention such that it differs from the raw, unmodified form as extracted from a plant. For example, starch can be modified by methods known in the art such as e.g., by inter alia chemical crosslinking and/or by stabilization through the introduction of anionic groups to the starch granule.

The term "microparticles", "microsphere" or equivalent expressions refer to a general designation for particles of a certain size, typically particle of a size that is less than or equal to about 50 microns (μm) at the widest point of the particle. In an exemplary embodiment, microparticles have a size that is less than or equal to about 45 microns (μm) at the widest point of the particle. In other exemplary embodiments, microparticles have a size that is less than or equal to about 40 microns (μm), less than or equal to about 35 microns (μm), less than or equal to about 30 microns (μm), less than or equal to about 25 microns (μm), less than or equal to about 20 microns (μm), less than or equal to about 15 microns (μm), less than or equal to about 10 microns (μm), and/or less than or equal to about 5 microns (μm), at the widest point of the particle. In still other exemplary embodiments, microparticles have a size that is less than or equal to about 4 microns (μm), less than or equal to about 3 microns (μm), less than or equal to about 2 microns (μm), less than or equal to about 1 micron (μm), less than or equal to about 0.5 micron (μm), less than or equal to about 0.4 micron (μm), less than or equal to about 0.3 micron (μm), less than or equal to about 0.2 micron (μm), and/or less than or equal to about 0.1 micron (μm). Thus, the term "starch foam microparticles" as used herein, refers to microparticles comprised of starch foam.

The term "foam" as used herein, refers to any substance comprising gas bubbles trapped in a liquid or in a solid. In an exemplary embodiment, foam is comprised of starch. Hence in an exemplary embodiment, foam is a starch foam. In one exemplary embodiment, starch foam is a solid foam. As is known in the art, solid foam compositions can have an open celled structure, a closed celled or have a structure that is a mixture of closed and open cells (see e.g., Glenn, G. M., et al. (1996) Microcellular Starch-Based Foams. In: G. Fuller, T. A. McKeon, D. D. Bills (Eds.) Agricultrual Materials as Renewable Resources. Pp. 88-106.). Open cell structured foams comprise pores that are connected to each other such that the connections form an interconnected network of pores. Closed cell foams do not have interconnected pores.

"Starch foam microparticles" have a porous structure that typically comprises a mostly, though not necessarily completely, open cell structure with a variety of cells/pores/bubble sizes. Typically, cells/pores/bubbles comprising a starch foam have a diameter that is less than or equal to about 10 microns (μm). In an exemplary embodiment, cells/pores/bubble sizes have a diameter that is in a size range that is between about 0.01 micron (μm) and about 2 microns (μm).

"Starch foam microparticles" can be spherical, or almost spherical or angular in shape. Populations of particles may comprise spherical starch foam microparticles, almost spherical starch foam microparticles, angular starch foam microparticles, or may be combinations of spherical, almost spherical and angular starch foam microparticles. Typically, the shape of starch foam microparticles depends on the method used for their manufacture. For example, spherical and/or almost spherical starch foam microparticles are formed when a starch melt is sprayed into a chamber containing ethanol. Angular starch particles are made by shearing a starch gel or starch melt in an ethanol solution using a high speed mixer.

The term "powder" as used herein, refers to a solid substance in the form of fine loose particles or granules. Typically powders comprise particles that are in a size range of between about 1 nm to about 1 mm. Starch foam microparticles comprising powders typically have a particle size that is less than or equal to about about 50 microns (μm) and equal to or greater than about 0.1 micron. In an exemplary embodiment, starch foam microparticles comprising powders have a particle size that is less than or equal to about 20 microns (μm).

The expression "free-flowing powder" as used herein refers to a powder of which the particles do not adhere significantly to one another and therefore the particles are able to move past one another essentially without restriction. Particles comprising a "free-flowing powder" do not clump together or otherwise agglomerate. Thus, a free flowing powder is one that flows consistently with minimal energy input. The inherent flowability of a powder is readily determined by methods known in the art (see e.g., U.S. Pat. No. 6,065,330, U.S. Patent Application Publication No. 20060070428, and *A Laboratory Handbook of Rheology*, Chapter III, Van Wazer et al., Interscience (1966)). Free-flowing powders comprising starch foam microparticles are readily mixed with other powders to make a homogenous mixture with other materials.

The expression "nonaqueous liquid" as used herein refers to a liquid substantially comprised of a nonaqueous solvent or mixtures of nonaqueous solvents. In an exemplary embodiment, the nonaqueous liquid comprises one or more polar solvents e.g., an alcohol, an ester, a ketone and/or an ether. In another exemplary embodiment, the nonaqueous liquid comprises one or more non-polar solvents e.g., toluene, xylene, benzene, acetone, hexane, octane, chloroform, and/or methylene chloride. In another exemplary embodiment, the non-aqueous liquid comprises at least one each of both polar and non-polar solvents.

In some exemplary embodiments, non-aqueous liquids also comprise water. In general, the water content of a nonaqueous liquid is less than the amount necessary to begin noticeably softening or dissolving the starch foam microparticles. Thus, in an exemplary embodiment, the amount of water present in a nonaqueous liquid is less than or equal to about 40% by weight based on the total weight of the nonaqueous liquid. For example, in some exemplary embodiments starch foam microparticles are equilibrated in a solution of 60% ethanol. In other exemplary embodiments, the water content of a nonaqueous liquid is less than or equal to about 30% by weight; less than or equal to about 20% by weight; less than or equal to about 10% by weight; less than or equal to about 5% by weight; and/or less than or equal to about 1% by weight. The exact amount of water present in a nonaqueous liquid is dependent on inter alia the nonaqueous liquid itself, the particular application for which the starch foam micoparticles are being used, and on the nature and composition of the starch comprising the starch foam microparticles e.g., whether the starch foam microparticles comprise unmodified starch, high amylose starch, or modified starch and/or the combination of modified and unmodified starches. Thus, having available the knowledge in the art and reference to the present disclosure, the exact amount of water in a nonaqueous liquid is readily determined by one of skill in the art.

The term "pharmaceutical" as used herein, refers to a medication e.g., a licensed drug, or substance taken for the purpose of curing, preventing or ameliorating symptoms of an illness or medical condition. The term "ameliorating" or "ameliorate" refers to any indicia of success in the treatment of a pathology or condition, including any objective or subjective parameter such as abatement, remission or diminishing of symptoms, making the condition more tolerable to the patient; making the final point of degeneration less debilitating, and/or an improvement in a patient's physical or mental well-being. Amelioration of symptoms can be based on objective or subjective parameters; including the results of a physical examination and/or a psychiatric evaluation.

The term "bee colony" or "honeybee colony" as used herein, refers to a social unit of bees, e.g., honeybees comprising a colony. The social unit can be any system of organization utilized by bees. Typically, colonies facilitate survival of the group. Thus, typically, a "bee colony" consists of groups of bees that cooperate in nest building, food collection, and brood rearing. Each member of a "bee colony" has a task to perform, and the combined efforts of the entire colony are directed to survival and reproduction. A colony typically has a single queen, thousands of workers, and hundreds of drones. Typically, the social structure of the colony is maintained by the queen and workers through an effective system of communication.

Domesticated honeybees are cultivated in "beehives" or "honeybee hives". Thus, the term "beehive" or "honeybee hive" refers to a structure that functions as a habitation for a colony of bees, e.g., a colony of honeybees.

The term "behavior modifying compound" as used herein refers to any substance or compound which influences the behavior or development of an organism e.g, stimulates a mating dance, and/or helps the organism find food, escape enemies and/or find a mate. Such substances can be naturally occurring or synthetically made. For example, "behavior-modifying compounds" include, but are not limited to e.g., semiochemicals such as e.g., pheromones, allomones, and kairomones.

The term "pheromone" as used herein, refers to a substance or mixture of substances which are secreted and released by an organism for detection and response by another organism of the same species. Pheromones mediate a variety of interactions between organisms. Thus, pheromones are typically classified by the interaction that they most strongly influence e.g., alarm, aggregation or sex pheromone.

As is known in the art, "pheromones" belong to the larger class of chemical compounds referred to as semiochemicals. The term "semiochemical" as used herein refers to chemicals that mediate interactions between organisms. Semiochemicals include allelochemicals and pheromones depending on whether the interactions are interspecific or intraspecific, respectively. As used herein the term "allelochemical" refers to chemical substances that induce a response in the receiver of the signal that is either adaptively favorable to the emitter but not the receiver (allomones), or that is favorable to the receiver but not the emitter (kairomones) or is favorable to both emitter and receiver (synomones). Allelochemicals and pheromones are useful e.g. as arrestants, attractants, repellents, deterrents, and/or stimulants.

The term "2-heptanone" or "heptane-2-one" as used herein, refers to a ketone that in its natural state is a component of the honey bee mandibular gland pheromone. 2-Heptanone is known in the art (see e.g., U.S. Pat. No. 6,843,985 which is incorporated herein by reference). In honey bees 2-Heptanone is a pheromone produced by the mandibular glands of adult worker honey bees, *Apis mellifera* and *Apis cerana* older than 8-10 days (see e.g., Vallet et al., J. Insect Physiol. 37(11):789-804 (1991); and Sakamoto et al., Journal of Apiculture Research 29(4):199-205 (1990) each of which are incorporated herein by reference).

The term "essential oil" as used herein refers to natural substances made by plants. Essential oils are found in many aromatic plants-herbs, flowers, and trees and are present in various parts of the plant including, but not limited to leaves, seeds, flowers, wood and bark. Typically, essential oils give the plant its particular signature scent. For example, oils such as lemon, orange, mustard, and anise give fruits and seeds their characteristic odor and taste. In Nature, the essential oils of plants have numerous functions for the plant which include, but are not limited to e.g., attracting bees for pollination, repelling insects, and/or protecting the plant from disease. Humans have invented many uses for essential oils including, but not limited to e.g., pesticides e.g., neem oil; insect and animal repellents e.g., citronella oil; food flavorings e.g., methyl salicylate (oil of wintergreen); and therapeutics e.g., lavender oil.

The term "biodegradable" as used herein refers to a composition or substance that decays and becomes absorbed by the environment. A biodegradable substance is capable of decaying through the action of living organisms typically, through the action of living organisms such as bacteria and fungi. Biodegradation of biodegradable substances such as food and sewage, typically leads to compaction and liquefaction, and to the release of nutrients that are then recycled by the ecosystem.

I. Introduction: Starch Foam Microparticles

In an exemplary embodiment the invention provides starch foam microparticles having a porous microcellular structure and a diameter at their largest point of less than or equal to about 50 μm. In an exemplary embodiment, the microparticles absorb about 25% weight/weight of non-aqueous liquid while remaining as distinct free flowing microparticles. Thus, in an exemplary embodiment, the loaded microparticles find use as free-flowing powders.

The powder form facilitates handling and packaging of the product on a commercial scale. Moreover, free-flowing powders are easily mixed and blended with other powders that may be needed as e.g., dietary supplements. Powders are less labor intensive to handle than other forms because they are easy to scoop from a container to apply and/or disperse e.g., in a honeybee colony.

In one aspect, the invention provides a free-flowing starch powder comprising starch foam microparticles that have a porous, mostly open cell structure. The starch foam microparticles absorb non-aqueous solutions and/or solvents while remaining, on the whole, as a free-flowing powder. In an exemplary embodiment, the starch foam microparticles absorb essential oils.

Starch, in its native form, is a free flowing powder. However, native starch powder is comprised of solid particles of starch. Although a thin film of non-aqueous liquid can be formed around each individual starch granule by mixing the native starch powder with a non-aqueous liquid, only a small percentage of the liquid can be loaded into the starch powder before the flow properties begin to change. Typically, for example, loading more than about 5% non-aqueous liquid (weight basis) onto native starch powder markedly affects the flowability and dispersion of the starch. Indeed, typically, loading more than about 5% non-aqueous liquid onto the starch particles results in agglomeration of the starch granules.

In an exemplary embodiment, the starch foam microparticles disclosed herein are able to be loaded with a much higher percentage of non-aqueous liquid (about 25% by weight) than are native starch powders, while still remaining as a free flowing powder. Without being bound by theory, it is believed that since the starch foam microparticles are porous, they are able to draw the non-aqueous liquid into the interior regions of the individual starch microparticles by capillary action. Thus, the non-aqueous liquid sequestered in the interior of the starch particle has little effect on the flow properties.

Starch foam microparticles have numerous uses including, but not limited to, providing an edible delivery system for feeding bees. In an exemplary embodiment, starch foam microparticles are used to feed bees nutritional oils. In another exemplary embodiment the starch foam microparticles are used to feed bees essential oils.

In still another exemplary embodiment, the starch foam microparticles are used to feed bees essential oils that have mitocidal properties. In another exemplary embodiment the essential oils with mitocidal properties are fed to the bees to control *Varroa* mites. Thus, the starch foam microparticles also provide a method for controlling *Varroa* mites in bee colonies.

In another exemplary embodiment, starch foam microparticles are loaded with a fragrance. In another exemplary embodiment, starch foam microparticles are loaded with a pharmaceutical. In another exemplary embodiment, starch foam microparticles are loaded with apheromone.

In one exemplary embodiment, starch foam microparticles are used to produce composite plastics. In another exemplary embodiment, composite plastics comprising starch foam microparticles are biodegradable. In another exemplary embodiment, the plastic composites are plastic films.

Starches

Starch is a complex plant carbohydrate used by plants to store excess glucose. All plants make starch. Starch typically occurs as a reserve polysaccharide in the leaf, stem, root (tuber), seed, fruit, and/or pollen of the plant. In its purified form, natural unmodified starch is a white tasteless and odorless powder.

Starch is frequently used in cooking for thickening sauces. In industry, starch typically is used e.g., in the manufacture of adhesives, paper, and textiles. Other exemplary uses of native starch is as a disintegrant in pharmaceutical tablets, and as a carrier for various substances.

Unmodified Starch

Biochemically, starch comprises two polymeric carbohydrates known in the art as amylose and amylopectin. Amylose is an $\alpha(1,4)$-linked glucose polymer which is essentially a linear chain without branching. Amylopectin on the other hand, is a branched glucose polymer in which branch chains are linked to the main chain of $\alpha(1,4)$-linked polymer by $\alpha(1,6)$-linkages.

As is known in the art, starch, in its raw state, is typically found in the form of solid, dense granules. The granules typically occur in a size range that is between about 2 microns (e.g., in wheat starch), to over about 100 microns (e.g., in potato starch (see e.g., Cameron and Donald (1992) Polymer 33:2628-2635)).

Starch granules hydrate in aqueous solution, swelling as much as about 10% in volume. Additional swelling occurs when an aqueous suspension of granules is heated, until a temperature is reached where there is a transition from organization to disorganization. This is known as the gelatinization temperature and typically occurs over a range of about 10° C.

In plants, native starch is synthesized by a series of enzymatic reactions (see e.g., Advances in Food and Nutrition Research, Vol. 41 supra; Martin and Smith (1995) Plant Cell. 7:971-985; Myers et al., (2000) Plant Physiol. 122:989-997). Genes or cDNAs of most starch biosynthetic enzymes from corn, potato, barley, and wheat have been cloned, and the cloned genes have been used to over- or under-express starch biosynthetic enzymes (see e.g., Stark, D. M., et al., (1992) Science 258:287; and Flipse, E., et al., (1994) Theor. Appl. Genet. 88:369). Thus, in an exemplary embodiment, starch foam microparticles comprise starch from a transgenic plant that expresses one or more cloned starch biosynthetic genes.

The relative proportions of amylose and amylopectin differ in starches derived from different species and different cultivars within species. For example, amylose content of wheat starch is about 0% for waxy wheat cultivars and about 22-30% (about 29% on average) for normal (non-waxy) wheat cultivars, and high amylose wheat cultivars are also known (see e.g., U.S. Pat. No. 7,001,939). In some maize cultivars the corn starch has an amylose content as high as about 60-70%.

The amylose and amylopectin content of starch can be measured by methods known in the art. In exemplary embodiments, amylose content is measured by the colorimetric methods (see e.g., Kuroda et al. Jpn. J. Breed. 39 (Suppl. 2):142-143, (1989)) and/or by amperometric titration (see e.g., Fukuba and Kainuma, "*Quantification of Amylose and Amylopectin*" in: Starch Science Handbook, Nakamura M. and Suzuki S., eds Tokyo: Asakura Shoten, pp174-179, (1977)). Starch concentration of solutions are determined by any method known in the art e.g., by the phenol-sulfuric acid method (Dubois et al., (1956) Anal. Chem. 28:350-356) with glucose as a standard.

Starch structures also differ in different species and in different cultivars within species. For example, barley and wheat amylopectins have larger portions of short branch chains (6 to 14 glucose units), and proportionally fewer branch chains of 11 to 22 glucose units when compared to e.g., maize amylopectin (see e.g., Jane et al., (1999) Cereal Chem. 76(5):629-637; and Song and Jane, (2000) Carbohydrate Polymers. 41:365-377).

In accordance with the differences in starch structure and composition, the size, shape, and gelatinization temperature of raw starch granules also vary based on the botanical source of the starch. For example, tapioca starch granules typically vary in diameter from between about 5 microns to about 35 microns, potato starch from between about 15 microns to about 100 microns, maize from between about 5 microns to about 25 microns, and rice starch granules vary from between about 3 microns to about 8 microns in diameter. Shapes typically include various, but are not limited to near perfect spheres, flattened ovoids, elongated disks, and polygons, and are characteristic of the source of the raw starch granule. Thus, a person of skill in the art can identify the plant source of a starch by observing the size and shape of the raw starch granule e.g., with the aid of a microscope.

As noted above, starch is found in nearly every type of plant tissue including, but not limited to the fruit, seeds, stems, leaves, rhizomes and/or tubers. Isolation of starch from plants is achieved by any of numerous methods well known in the art. Exemplary methodology is disclosed in e.g., Advances in Food and Nutrition Research, Vol. 41 supra; *Starch Chemistry and Technology*, R. L. Whistler ed., Academic Press (1984); and *Starch: Properties and Potential*, Galliard, T., ed., John Wiley and Sons (1987).

Modified Starch

Modified starch refers to starch that has been treated in order to modify one or more of its physical or chemical properties. Modification is brought about by any means known in the art e.g., including, but not limited to chemical modification, physical modification, modification by biotechnological methods, and traditional plant breeding methods (see e.g., *Starch in Food: Structure, Function and Applications*, Ann-Charlotte Eliasson, Ed. CRC Press, 2004).

Chemical modification typically alters the arrangement of glucose chains in the starch granules, and/or introduces additional chemical groups to the starch e.g., phosphate. Chemical modification can be achieved by any method known in the art (see e.g., Tomasik P, and Schilling CH. (2004) Adv. Carbohydr. Chem. Biochem. 59:175-403). Physical processes, e.g., heat, are also used to modify the characteristics of the starch. Starch is also frequently modified enzymatically, e.g., to promote reorganization of the glucose chains in the starch. Traditional plant breeding and modern biotechnology methods are also used to modify starch. For example in exemplary embodiments breeding methods are used to manipulate the type of starch made by different plants e.g., by modifying the enzymes responsible for making the "branches" in amylopectin to influence the structure of the amylopectin made by the plant.

Exemplary modified starches include, but are not limited to pregelatinized starches, acid modified starches, cationic starches, starch esters, cross-linked starches, hypochlorite-oxidized starches, hydroxyalkyl starches and/or starch phosphate monoesters.

Starch Foam Microparticles

In an exemplary embodiment, the invention provides starch foam microparticles. Starch foam microparticles comprise porous solid starch foam comprised of a network of air-filled cells/pores. In an exemplary embodiment, starch foam microparticles absorb non-aqueous liquids and after doing so, the population of starch foam microparticles remains as a free flowing powder.

Although starch, in its native form, is a free flowing powder native starch powder is distinguished from powders comprising starch foam microparticles by virtue of the fact that native starch powder is comprised of solid particles of starch whereas, in contrast, starch foam microparticles are a porous foam.

In one exemplary embodiment, starch foam microparticles have a diameter of less than or equal to about 50 microns (μm) at their widest point. In one exemplary embodiment, a population of starch foam microparticles of a specified size e.g., a population of starch foam microparticles that are at less than or equal to about 50 μm diameter at their widest point, is a population wherein at least about 75% of the starch foam microparticles comprising the population are of the specified size. In other exemplary embodiments, at least about 80%, at least about 85%, at least about 90%, at least about 91%, at least about 92%, at least about 93%, at least about 94%, at least about 95%, at least about 96%, at least about 97%, at least about 98%, at least about 99%, at least about 100%, of the starch foam microparticles comprising the population are of the specified size. In other exemplary embodiments, starch foam microparticles have a diameter of less than or equal to about 45 μm, less than or equal to about 40 μm, or less than or equal to about 35 μm. In another exemplary embodiment, starch foam microparticles have a diameter of less than or equal to about 30 μm. In another exemplary embodiment, starch foam microparticles have a diameter of less than or equal to about 25 μm. In another exemplary embodiment, starch foam microparticles have a diameter of less than or equal to about 20 μm. In other exemplary embodiments, starch foam microparticles have a diameter of less than or equal to about 15 μm, about 10 μm, or about 5 μm. In still other exemplary embodiments, starch foam microparticles have a diameter of less than or equal to about 4 μm, about 3 μm, about 2 μm, about 1 μm, about 0.5 μm, or about 0.1 μm.

Starch foam microparticles are low density. Native starch granules have a density that is typically about 1.4 $g/cm^3$ or more. Starch foam microparticles are porous, and thus typically have a density that is less than about 1.4 $g/cm^3$. Typically, the density of starch foam microparticles is in a range that is less than about 1.3 $g/cm^3$ and greater than or equal to about 0.10 $g/cm^3$. In one exemplary embodiment, starch foam microparticles have a density that is less than or equal to about 1.0 $g/cm^3$. In another exemplary embodiment, starch foam microparticles have a density that is less than or equal to about 0.75 $g/cm^3$. In other exemplary embodiments, starch foam microparticles have a density that is less than or equal to about 0.60 $g/cm^3$, less than or equal to about 0.50 $g/cm^3$, less than or equal to about 0.40 $g/cm^3$, or less than or equal to about 0.35 $g/cm^3$. In another exemplary embodiment, starch foam microparticles have a density that is in a range that is between about 0.14 $g/cm^3$ to about 0.34 $g/cm^3$. In another exemplary embodiment, starch foam microparticles have a density that is less than or equal to 0.32 $g/cm^3$. In other exemplary embodiments, starch foam microparticles have a density that is less than or equal to about 0.30 $g/cm^3$, and/or less than or equal to about 0.20 $g/cm^3$.

In an exemplary embodiment, starch foam microparticles are used as carriers for non-aqueous liquids. Native starch particles can be loaded with a thin film of non-aqueous liquid. However, only a small percentage of the non-aqueous liquid can be loaded into the native starch powder before the flow properties of the powder begin to change. Typically, for native starch powders, the amount of non-aqueous liquid that can be loaded onto a native starch granule is about 5% on a weight basis. In contrast, in an exemplary embodiment, starch foam microparticles can be loaded with at least about 25% non-aqueous liquid on a weight basis, and still remain a free-flowing powder. Thus, in one exemplary embodiment, starch foam microparticles are loaded with a non-aqueous liquid e.g., one or more essential oils. In one exemplary embodiment, the non-aqueous liquid is a food for honey bees. In another exemplary embodiment, the non-aqueous liquid is a mitocide. In another exemplary embodiment, the non-aqueous liquid is a pharmaceutical. In another exemplary embodiment, the non-aqueous liquid is a fragrance.

In another exemplary embodiment, starch foam microparticles are used as fillers in plastic composites.

Production of Starch Foam Microparticles

Starch foam microparticles are typically prepared from a starch melt. Once formed, the starch melt is treated to exchange the water in the melt with air. The exchange takes place under conditions that minimize the effects of surface tension and thus maintain the integrity of the network of cells in the foam structure (see e.g., Glenn and Irving (1995) *Cereal. Chem.* 72, 155-161 and U.S. Pat. No. 5,958,589; Microcellular Starch Based Foams. In *Agricultural Materials as Renewable Resources*; Fuller, G., McKeon, T. A., Bills, D. D., Eds., ACS Symposium Series 647, American Chemical Society, (1996) 88-106; and Glenn and Irving, supra).

Although starch foam microparticles can be produced by any method known in the art, in an exemplary embodiment, solvent exchange is used to provide conditions that minimize the effects of surface tension and maintain the integrity of the network of cells in the foam structure. Any suitable solvent may be used for solvent exchange. In an exemplary embodiment the solvent is a water miscible solvent. In one exemplary embodiment, the water miscible solvent is an alcohol e.g., methanol, ethanol, isopropanol. In another exemplary embodiment the water miscible solvent is a ketone e.g., acetone, ethyl acetate.

Typically, as noted above, starch foam microparticles are prepared by first forming a starch melt. In an exemplary embodiment, the initial concentration of starch to water for forming a melt is in a range of concentration that is between about 1% to about 20% starch, weight by volume. In other exemplary embodiments, the concentration range varies according to the type of starch used. The exact amount for any given application is readily determined by one of skill in the art e.g., by way of trial runs, having the benefit of this disclosure.

In one exemplary embodiment, the starch is unmodified wheat starch, and the concentration of starch to initial water in the melt is between about 6% to about 10% weight by volume. In another exemplary embodiment, the concentration of unmodified wheat starch is about 8%. In another exemplary embodiment, the starch is unmodified high amylose starch e.g., high amylose corn starch, high amylose wheat starch etc. In one exemplary embodiment, the concentration of unmodified high amylose starch to initial water for preparation of a melt is in a range that is between about 5% to about 8%. In another exemplary embodiment, the concentration of unmodified high amylose starch is about 8%. In another exemplary embodiment, the concentration of starch in the suspension is in a range that is between about 2% to about 5% by weight.

Figure 1:
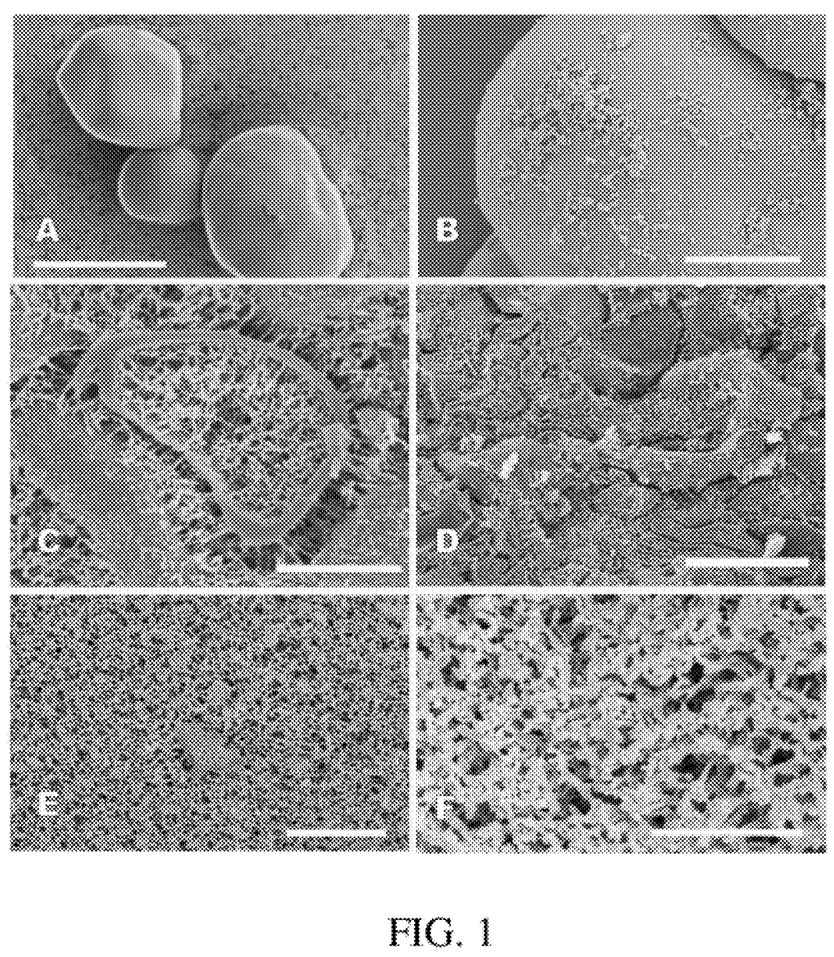
Figure 2:
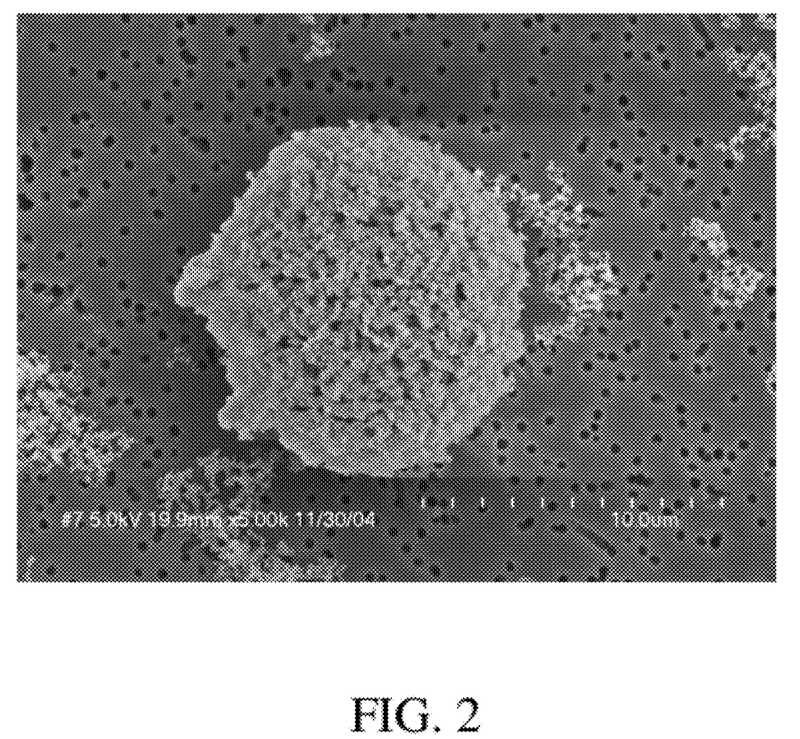
FIG. 2. A starch sphere from corn starch made by spraying the starch melt into ethanol and then dehydrating and drying the sample. Note the absence of starch granule remnants or envelopes.

Starch foam microparticle size is influenced by the temperature at which the melt is processed. For example, in FIG. 1(C) the scanning electron micrograph illustrates that when starch is heated in water to a temperature of about 95° C., for about 30 minutes, the starch gelatinizes but leaves a swollen starch envelope or remnant that is larger than the size of the original starch granule. Without being bound by theory, it is believed that the starch granule remnant limits the particle size that may be obtained. Typically, heating the starch melt to over about 100° C. e.g., 101° C., 102° C., 103° C., 104° C., 105° C., 106° C., 107° C., 108° C., 109° C., or more, will completely dissolve the envelope and allow the formation of smaller microparticles (typically less than or equal to about 50 microns (μm)). Higher temperatures e.g., at least about 110° C., 111° C., 112° C., 113° C., 114° C., 115° C., 116° C., 117° C., 118° C., 119° C., or 120° C. cf FIG. 1(F), or more, up to about 150° C., completely dissolve all starch granule remnants. Thus, the particle size can be reduced to a still smaller diameter e.g., typically less than or equal to about 40 μm, less than or equal to about 30 μm, less than or equal to about 20 μm, less than or equal to about 10 μm, less than or equal to about 5 μm, less than or equal to about 1 μm, and/or less than or equal to about 0.5 μm. In general, the higher the temperature used to form the melt, the smaller and tighter the size range of microparticles obtained. However, starch will begin to degrade at temperatures above 200° C. Therefore, to achieve the smallest starch particles one of skill in the art would appreciate that the temperature should be high enough to dissolve the starch envelope, but low enough to prevent degradation of the starch e.g., around 120° C.

In an exemplary embodiment, starch microparticles are made by pumping the starch melt through an atomizing nozzle to form very small droplets. In this embodiment, viscosity of the starch melt is kept low to facilitate pumping of the melt through the atomizing nozzle. In an exemplary embodiment, the concentration of starch is in a range that is between about 2% to about 5%. In this embodiment, the droplets fall from the nozzle by gravity into a container of water miscible solvent e.g., an alcohol, and are there collected and further dehydrated in additional changes of solvent. Typically, this method produces spherical, or approximately spherical porous starch foam microparticles.

In another exemplary embodiment, the starch melt is formed as disclosed above, and then the resulting melt is poured into a container and allowed to cool and gel. In an exemplary embodiment the starch concentration is in a range that is between about 8% to about 12%. The gel is then placed in a container of water miscible solvent and thoroughly sheared with a high-speed mixer. The shear-formed particles are further dehydrated in additional changes of water miscible solvent. Typically this method produces starch foam microparticles that are angular in shape.

Loading Starch Foam Microparticles with Non-Aqueous Liquid

Starch foam microparticles are loaded with non-aqueous liquids by any method known in the art. In an exemplary embodiment, starch foam microparticles are mixed with non-aqueous liquid and allowed to absorb the liquid. In one exemplary embodiment the non-aqueous liquid comprises a mixture of non-aqueous liquids. In another exemplary embodiment the non-aqueous liquid comprises a carrier liquid that is evaporated off after loading of the starch microparticles.

In one exemplary embodiment, starch foam microparticles are loaded with 25% non-aqueous liquid by mixing a powder comprising starch foam microparticles with non-aqueous liquid such that the non-aqueous liquid comprises about 25% of the mixture. The mixture is allowed to stand in order to allow the starch foam microparticles to absorb the liquid. In another exemplary embodiment, starch foam microparticles are loaded with about 24% non-aqueous liquid, about 23% non-aqueous liquid, about 22% non-aqueous liquid, about 21% non-aqueous liquid, 20% non-aqueous liquid by mixing a powder comprising starch foam micro particles with non-aqueous liquid such that the non-aqueous liquid comprises 20% of the mixture. In other exemplary embodiments, starch foam microparticles are loaded with about 19% non-aqueous liquid, about 18% non-aqueous liquid, about 17% non-aqueous liquid, about 16% non-aqueous liquid, about 15% non-aqueous liquid, about 14% non-aqueous liquid, about 13% non-aqueous liquid, about 12% non-aqueous liquid, about 11% non-aqueous liquid, about 10% non-aqueous liquid, or less than about 10% non-aqueous liquid. Similarly, in other embodiments starch foam microparticles are loaded with a non-aqueous liquid by mixing the desired amount of non-aqueous liquid to be loaded with an appropriate amount of powder comprising starch foam microparticles.

Powders

Particulate and powdered materials are useful in a wide variety of situations. For example, free-flowing powders facilitate the handling and packaging of product on a commercial scale. Free-flowing powders are also easily mixed and blended with other powders. Powders are easy to scoop from a container and are easy to apply and disperse e.g., in a honeybee colony. Thus, from an application perspective, powders are easier and less labor intensive to handle than other solid forms e.g., solid blocks.

As is known in the art, powders have numerous measurable physical properties including e.g., properties associated with the particles e.g., particle size distribution, particle density; and bulk powder properties e.g., flowability.

Flowability is an exemplary bulk property of powders. Numerous factors affect the flowability e.g., humidity, moisture absorption, and aeration. For example, with many powders, the addition of excess air (aeration) reduces packing density as well as the interparticulate forces, thereby improving flowability of the powder. In contrast, exposure to moisture tends to reduce flowability since the moisture displaces the air, and increases the various cohesive forces between particles of the powder. In some cases where the particle is capable of moisture absorption itself, the particle weight may also increase. Thus, exposure to moisture typically decreases flowability. Powder flowability is readily measured by one of skill in the art using known methods (see e.g., U.S. Pat. No. 6,065,330, U.S. Patent Application Publication No. 20060070428, and *A Laboratory Handbook of Rheology*, Chapter III, Van Wazer et al., Interscience (1966)).

In one exemplary embodiment, the invention provides a powder comprising starch foam microparticles wherein the starch foam microparticles absorb at least about 25% by weight of a non-aqueous liquid and the powder remains free flowing.

In another exemplary embodiment, powders comprising starch foam microparticles having a small particle size e.g., microparticles that are less than or equal to 20 microns in diameter at their widest point, facilitate ingestion by honeybees. In another exemplary embodiment powders comprising starch foam microparticles are used in the production of composite films. In another exemplary embodiment, powders comprising starch foam microparticles are used as chemical delivery systems. In another exemplary embodiment, powders comprising starch foam microparticles are used in pharmaceutical compositions.

Chemical Delivery Systems

In exemplary embodiments the starch foam microparticles are chemical delivery systems. The delivery system can be used with any non-aqueous chemical e.g., an oil, 2-heptanone, hexane, alcohol etc. . . . . Thus, in an exemplary embodiment, the starch foam microparticles provide a chemical delivery system for an oil. In another exemplary embodiment, the starch foam microparticles are chemical delivery system for an essential oil. In another exemplary embodiment, the starch foam microparticles provide a chemical delivery system for agrochemical e.g., 2-heptanone. In another embodiment the starch foam microparticles are chemical delivery system for at least one chemical effective for controlling *Varroa* mites in bee colonies.

Oils

In exemplary embodiments the starch foam microparticles are loaded with at least one oil. The oil is either a volatile or non-volatile oil. In an exemplary embodiment the oil is a carrier oil for a volatile chemical. In another exemplary embodiment, the oil is a member selected from the group consisting of a vegetable oil, a petroleum based oil, a synthetic oil, and a plant extracted oil. In another exemplary embodiment, the oil is a volatile oil, e.g., an essential oil.

Essential Oils

Essential oils, also known as ethereal plant oils, are natural substances found in many aromatic plants-herbs, flowers, and trees. Essential oils are present in various parts of the plant e.g., leaves, seeds, flowers, and bark and give the plant its particular signature scent. In Nature, plants produce essential oils to e.g., attract bees for pollination, to repel insects, and to help protect the plant from disease. As is known in the art, extracted essential oils, are typically produced in the form of concentrated, hydrophobic liquids that comprise the volatile aromatic compounds from the plant. Extracted essential oils offer a wide range of therapeutic and other possibilities for human use (see e.g., E. Guenther, The Essential Oils, vol. 4, Van Nostrand, N.Y., (1950) and E. Guenther, The Essential Oils, vol. III (Van Nostrand, N.Y., 1949)). Essential oils can be obtained by any method known in the art e.g., essential oils can be extracted or manufactured.

In an exemplary embodiment, catnip oil is absorbed by/loaded onto the starch foam microparticles. In one exemplary embodiment, catnip oil is absorbed by/loaded onto the starch foam microparticles and used to attract honeybees.

In one exemplary embodiment, cinnamon oil is absorbed by/loaded onto the starch foam microparticles. In another exemplary embodiment cinnamon oil is absorbed by/loaded onto the starch foam microparticles and used an attractant for bees. In another exemplary embodiment cinnamon oil is absorbed by/loaded onto the starch foam microparticles as an attractant for bees and as a miticidal agent. In another exemplary embodiment cinnamon oil is absorbed by/loaded onto an insecticide. In another exemplary embodiment cinnamon oil is absorbed by/loaded onto a fragrance/perfume.

In one exemplary embodiment, clove oil, is absorbed by/loaded onto the starch foam microparticles.

In another exemplary embodiment, camphor oil is absorbed by/loaded onto the starch foam microparticles.

In another exemplary embodiment, Citronella Oil, which in an exemplary embodiment, is obtained from fresh grass of *Cymbopogon* species e.g., *Cymbopogon nardus* is absorbed by/loaded onto the starch foam microparticles. In one exemplary embodiment, citronella oil is a perfume/fragrance. In another exemplary embodiment, citronella oil is an insect repellent.

In another exemplary embodiment, eucalypt oil, or dinkum oil, which in an exemplary embodiment, is obtained from fresh leaves of *Eucalyptus* species e.g., *Eucalyptus globulus*, is absorbed by/loaded onto the starch foam microparticles. In an exemplary embodiment eucalypt oil is an inhalation expectorant.

In another exemplary embodiment, patchouli oil, which in an exemplary embodiment, is obtained from *Pogostemon* species e.g., *Pogostemon cablin* is absorbed by/loaded onto the starch foam microparticles. In an exemplary embodiment, patchouli oil is a perfume. In another exemplary embodiment, patchouli oil is an insect repellent. In another exemplary embodiment patchouli oil is a miticidal agent.

In another exemplary embodiment, peppermint oil, which in an exemplary embodiment, is obtained from *Mentha* species e.g., *Mentha piperita*, is absorbed by/loaded onto the starch foam microparticles.

In another exemplary embodiment, rosemary oil, which in an exemplary embodiment, is obtained from *Rosmarinus* species, is absorbed by/loaded onto the starch foam microparticles.

In another exemplary embodiment, spearmint oil which in an exemplary embodiment, is obtained from *Mentha* species e.g., *Mentha spicata*, is absorbed by/loaded onto the starch foam microparticles.

In another exemplary embodiment, tea tree oil, which in an exemplary embodiment, is obtained from leaves of *Melaleuca* species e.g., *Melaleuca alternifolia* is absorbed by/loaded onto the starch foam microparticles. In one exemplary embodiment, tea tree oil is dispensed by the starch foam microparticles as a miticidal agent. In another exemplary embodiment tea tree oil is dispensed by the starch foam microparticles as an attractant for bees and as a miticidal agent. In still another exemplary embodiment, tea tree oil is an insecticide.

In another exemplary embodiment, thyme oil, which in an exemplary embodiment, is obtained from *Thymus* species e.g., *Thymus vulgaris*, is absorbed by/loaded onto the starch foam microparticles. In one exemplary embodiment thyme oil is absorbed by/loaded onto the starch foam microparticles as a miticidal agent. In another exemplary embodiment thyme oil is an attractant for bees and a miticidal agent. In another exemplary embodiment thyme oil is an insecticide.

In another exemplary embodiment, wintergreen oil, is absorbed by/loaded onto the starch foam microparticles. In one exemplary embodiment wintergreen oil is a miticidal agent. In another exemplary embodiment wintergreen oil is an attractant for bees and a miticidal agent. In another exemplary embodiment wintergreen oil is an insecticide.

In some exemplary embodiments, more than one essential oil is combined to make a mixture that is absorbed by/loaded onto the starch foam microparticles. In one exemplary embodiment, the mixture comprises clove oil. In another embodiment, the mixture comprises thyme oil. In another embodiment, the mixture comprises clove oil and thyme oil.

In other embodiments sweet almond oil, apricot kernel oil, grapeseed oil, avocado oil, peanut oil, olive oil, pecan oil, macadamia nut oil, sesame oil, evening primrose oil, walnut oil and wheat germ oil are carrier oils absorbed and/or dispensed by the starch foam microparticles.

Honey Bees

An exemplary application for starch foam microparticles is in the honeybee industry. Bees are insects of the order Hymenoptera, Superfamily Apoidea, and comprise a group of about 20,000 species of bees that live throughout the world. Honeybees are of the genus *Apis* and belong to the family Apidae. At least four species of honeybee are commonly recognized: the dwarf, or midget, bee *Apis florae*; the giant, or rock, bee *Apis dorsata*; the oriental (Indian, Chinese, Japanese, etc.) bee *Apis cerana*; and the common (European, African, etc.) honey-bee *Apis mellifera*. The existence of another giant bee, *Apis laboriosa*, has recently been confirmed.

Honeybees, in particular *Apis mellifera*, are the primary pollinators of most commercial crops in North America, and are the most widely used and actively managed pollinators in the world. Indeed, *Apis mellifera* produce more than $270 million of honey and wax and pollinate over $14 billion of crops annually in the U.S. alone. Thus, honeybees have a significant economic impact, and therefore, maintaining healthy bee colonies is an essential aspect of much agricultural practice.

Unfortunately, a serious threat to honeybees is the parasitic mite, *Varroa destructor*. *Varroa* mites deform developing bees, cause weight loss and premature death and transmit various viral diseases. *Varroa* mite infestations can completely destroy infected honeybee colonies in as little as a few weeks when remedial measures are not taken. Indeed, beekeepers and the beekeeping industry worldwide have reported epidemic losses of managed bee colonies ranging from 25 to 80% (see e.g., U.S. Pat. No. 6,843,985; Oldroyd, B. P. (1999) *Tree* 14(8):312-315; Contzen, C. et al. (2004) *Thermochimica Acta*, 415:115-121; and De Jong, D. et al. (1982) *J. Apic. Res.*, 21:165-167). Thus, *Varroa destructor* has had a catastrophic effect on populations of managed and feral honey bee colonies.

Naturally, beekeepers and the beekeeping industry have taken steps to attempt to control infestations of *Varroa*. Current methods include, but are not limited to biotechnical, genetic and chemical means (see e.g., Kanga, L. H. B. et al. (2002) *Journal of Invertebrate Pathology* 81, 175-184). Biotechnical methods include, but are not limited to measures such as mite trapping devices. While trapping devices are effective, they are also labor intensive and not particularly efficient (Kanga supra). Chemical means of control include, but are not limited to an EPA-registered plastic strip impregnated with the contact pyrethroid pesticide, fluvalinate (Apistan® strips). Unfortunately however, some populations of *Varroa* have shown resistance to this pesticide (see e.g., Elzen, P. J. and Westervelt, D. (2002) *American Bee Journal* 142(4):291-292; Elzen, et al. (1999) *Apidologie* 30(1):13-17; and Macedo, P. A et al. (2002) *American Bee Journal* 142(7): 523-526).

The organophosphate coumaphos (CheckMite+®) has been used to control fluvalinate-resistant *Varroa*, but mites resistant to coumaphos are already evident (Elzen & Westervelt 2002 supra), and there are a number of sites across the U.S. where *Varroa* appears to be resistant to both coumaphos and fluvalinate (see e.g., Elzen, G. W. (2001), In *Biopesticides and Pest Management*, Campus Books International, New Delhi. pp. 258-261). Furthermore, fluvalinate and coumaphos are lipophyllic and can contaminate honey, beeswax and other hive products (see e.g., Wallner, K. (1999) *Apidologie* 30:235-248).

Therefore, what is needed in the art are effective methods for controlling *Varroa* that are non-toxic to humans and to which the mites do not readily become resistant.

Ethereal plant oils, also known as essential oils, are known in the art to be capable of controlling bee mites (see e.g., Calderone et al. (1997) *J. Econ. Entomol.* 90:1060-1086; Colin M. E. (1990) J. Applied Entomol. 110:19-25; Imdorf et al. (1999) *Apiacta* 32(3):89-91; Sammataro et al. (1998) *Amer. Bee J.* 138:681-685). Indeed, essential oils e.g., clove, thyme, wintergreen, patchouli, tea tree oil, or combinations thereof, can either kill, or adversely affect *Varroa* mites thereby facilitating their control and/or elimination from bee colonies.

Commercial products that incorporate essential oils have been developed. One exemplary commercial essential oil product, Apivar® (thymol and camphor based), is available in the United States for *Varroa* control. Apivar® is designed to create a plume of oil vapors that kill the *Varroa* on adult bees. Unfortunately however, vapor-phase oil products tend to exhibit a high variation in oil volatility under different environmental conditions. Consequently, mite control with a vapor phase delivery system is unpredictable. Thus, prior to the discovery and development of the starch foam microparticles disclosed herein, a predictable system for effective delivery of essential oils to bee colonies did not exist.

Therefore, in an exemplary embodiment, the invention provides starch foam microparticles that absorb a non-aqueous solution comprising at least one essential oil that is effective for controlling *Varroa* mites. In another exemplary embodiment, essential oils are loaded on the starch foam microparticles at an amount of about 25% weight/weight. In another exemplary embodiment essential oils are loaded on the starch foam microparticles at an amount of about 24% weight/weight. In other exemplary embodiments essential oils are loaded on the starch foam microparticles at an amount of about 23% weight/weight, about 22% weight/weight, about 21% weight/weight, about 20% weight/weight, about 19% weight/weight, about 18% weight/weight, about 17% weight/weight, about 16% weight/weight, about 15% weight/weight, about 14% weight/weight, about 13% weight/weight, about 12% weight/weight, about 11% weight/weight, about 10% weight/weight, about 9% weight/weight, about 8% weight/weight, about 7% weight/weight, and/or about 6% weight/weight.

In other exemplary embodiments, essential oils are loaded on the starch foam microparticles at an amount at an amount of about 5% weight/weight, about 4% weight/weight, about 3% weight/weight, about 2% weight/weight, about 1% weight/weight, and or about 0.5% weight/weight. In one exemplary embodiment, loading about 25% essential oils by weight, the starch foam microparticles remain in the form of a free flowing powder that exhibits no clumping.

Bees readily consume particles that are small enough to get into and traverse the proboscis. Typically, for easy consumption by bees, the particle is equal to or smaller than about 20 µm. Fortunately, in exemplary embodiments, the starch foam microparticles are small enough for bees to eat. Thus, in one exemplary embodiment, starch foam microparticles are equal to or less that about 20 µm in diameter at their widest point.

In an exemplary embodiment, the loaded, free flowing starch foam microparticles are mixed with other bee attractants e.g., powdered sugar, and the resulting mixture is fed to the bees. Without being bound by theory it is believed that bees utilize the particles and the encapsulated oils as a source of food, and the ingested oil provides systemic control of the parasitic mites.

In one exemplary embodiment, *Varroa* mites are killed by direct contact with at least one essential oil that is fed to the bees in the form of loaded starch foam microparticles. In this embodiment, mites come in contact the starch encapsulated oils on the exterior of the bee, much the same way mites pick up cuticular hydrocarbons from the bees on a routine basis. Thus, in an exemplary embodiment, when the bees are fed the starch foam microparticle encapsulated oils, the mites pick up a low level of the oils from contact with the bees, and are incapacitated.

In another exemplary embodiment, *Varroa* mites are controlled by impaired reproduction. In this exemplary embodiment, the starch foam microparticles comprising at least one essential oil are ingested by nurse bees. When the nurse bees feed larvae, essential oils in the bee milk and communal food are ingested by the larvae. When female *Varroa* mites feed on treated larvae or larval food at the bottom of the cell, they ingest the essential oils and this adversely affects their reproduction. In one exemplary embodiment, reproduction is adversely affected when the female mites are unable to lay eggs. In another exemplary embodiment, reproduction is adversely affected when the essential oils are present in lower concentrations, which allows the females to lay eggs, but delays development of immature mites and thus, ultimately results in death of the mites while they are still immature. Thus, starch foam microparticles provide means for systemically controlling of *Varroa* mites in bees and in bee colonies using essential oils.

In another exemplary embodiment, starch foam microparticles absorb a chemical that is not an essential oil, and that has miticidal properties e.g., pyrethroids, organophosphates, and/or 2-heptanone. In an exemplary embodiment, 2-Heptanone is absorbed by the starch foam microparticles. 2-Heptanone vapor acts as an attractant for *Varroa* mites at low concentrations but has miticidal properties at higher concentrations (see e.g., U.S. Pat. No. 6,843,985).

Thus, in exemplary embodiments, starch foam microparticles microparticles provide a food source, both alone and empty and/or in combination with an essential oil, and at the same time loaded starch foam microparticles are used to control infestations of *Varroa* mite in honeybees and honeybee colonies.

Pharmaceuticals

In an exemplary embodiment starch foam microparticles are a carrier for a pharmaceutical. In one exemplary embodiment starch foam microparticles provide a vehicle oral administration of pharmaceutical compositions to persons in need thereof e.g., as particles within a capsule. However, many drugs have to be administered by injection, since they are either subjected to degradation or are insufficiently absorbed when they are administered orally, nasally or by the rectal route. A drug preparation intended for parenteral administration should be biocompatible and biodegradable and the degradation products should be non-toxic. In addition, particulate drugs intended for injection should be small enough to pass through an injection needle. Typically particulate drugs intended for injection are smaller than 200 μm at their widest point. Therefore, in another exemplary embodiment, starch foam microparticles provide a vehicle for parenteral administration of pharmaceutical compositions to persons in need thereof.

Starch foam microparticles can be used with any nonaqueous formulation/preparation/emulsion of at least one pharmaceutical e.g., Anti-asthmatics e.g., Terbutaline; Antibacterials e.g., penicillin; Antifungals e.g., Fluconazole; Anti-inflammatory agents e.g., Benzidamine, Pyroxicam; Antivirals e.g., Acyclovir.

Fragrance Dispensers

People perceive objects and other people to a significant degree in part through their sense of smell, and their behavior is profoundly affected by this. Even small concentrations of aromas can influence people's moods and, consequently, their behavior. Therefore, in an exemplary embodiment the invention provides starch foam microparticles that absorb a volatile chemical or substance, wherein the chemical or substance is fragrant to humans e.g., an essential oil or synthetic perfume e.g., "Pleasures" by Este Lauder.

Plastic Products and Plastic Films

Fillers are routinely used in making plastic composite films and injection molded articles. One recent technological breakthrough in the plastics industry is the development of polymer nanocomposites, i.e. plastics resins reinforced with nanosize additives. The properties of nano-composite materials are influenced by the properties of the individual starting materials and their morphology and interfacial characteristics. Thus, in an exemplary embodiment, starch foam microparticles are used as a filler in composite plastic products e.g., thermoformed plastic products, and/or extruded plastic products. Thermoformed plastic products are known in the art (see e.g., co-pending U.S. patent application Ser. No. 11/431,496 filed May 9, 2006). Plastic composite products comprising starch foam microparticles can be formed into any shape or form e.g., squares, circles, triangles, rectangles, cubes, pyramids, stars, chairs, loungers, beds, boxes, spheres, boats, rods, beams, balls, cones, u-shape, horseshoe, animal, car, plant, insect, etc, that is, any convenient and/or desirable shape.

Particle size of the filler is an important parameter in determining how much filler can be added to a plastic while still retaining the functionality of the material. Particle size is particularly important in plastic films because of the extremely small sample thickness of a film. For example, a large filler particle that spanned the thickness of the film would create a weak point in the film. Thus large particles are not an ideal choice for composite plastic films.

In contrast, very small particles can be added without compromising the film properties since the small particles will not span the thickness of the film. Furthermore, fillers with very small particles can be added in greater amounts without compromising the film properties because the small particles will not span the thickness of the film. Additionally, small particles that can form a very strong interaction with the polymer chains produce a composite matrix with enhanced performance.

Therefore, in an exemplary embodiment, the invention provides starch foam microparticles for the manufacture of composite plastic films. In one exemplary embodiment, the invention provides starch foam microparticles for the manufacture of composite plastic films, wherein the starch foam microparticles are less than or equal to about 50 microns in diameter at their widest point. In another exemplary embodiment, the invention provides starch foam microparticles for the manufacture of composite plastic films wherein the starch foam microparticles have a diameter at their widest point which is in the nanometer range e.g., about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, and/or about 999 nm. In another exemplary embodiment, starch powders comprising starch foam microparticles having a diameter at their widest point which is in the nanometer range, are added in an amount that is less than or equal to about 50% on a weight basis to plastic for the purpose of making composite plastic films. Thus, in exemplary embodiments, starch foam microparticles having a diameter at their widest point which is in the nanometer range, are added in an amount that is about 50% on a weight basis, about 45% on a weight basis, about 40% on a weight basis, about 35% on a weight basis, about 30% on a weight basis, about 25% on a weight basis, about 20% on a weight basis, about 15% on a weight basis, about 10% on a weight basis, about 5% on a weight basis, about 1% on a weight, or less than about 1% on a weight basis, to plastic for the purpose of making composite plastic films. In another exemplary embodiment, the invention provides starch foam microparticles for the manufacture of composite plastic films wherein the starch foam microparticles have a diameter at their widest point which is less than or equal to about 25% the thickness of the film.

In another exemplary embodiment, the invention provides starch foam microparticles that have improved interfacial interactions with plastic materials. Improved interfacial interactions can be achieved by any method known in the art (see e.g., WO03/074604 and Vinidiktova, N. S., et al. (2006) Mechanics of Composite Materials 42:273-282). In another exemplary embodiment, the invention provides starch foam microparticles comprising modified starch, wherein the modification improves the interfacial interaction between the starch foam microparticles and the plastic. Modifications to improve interfacial interactions are known in the art (see e.g., Vinidiktova, N. S., et al. supra). Starch foam microparticles can be added to any plastic known in the art e.g., polyethylene, polyvinyl chloride, polyvinylidene chloride, polystyrene, polypropylene, plastarch material, polylactic acid, polyhydroxybutyrate and/or combinations of these or any known plastics.

The following examples are offered to illustrate, but not to limit the invention.

EXAMPLES

Example 1

Preparation of Starch Foam Microparticles I

The following example illustrates one exemplary method by which starch foam microparticles are produced.

Temperature treatments were performed using a 1 L pressure reactor (Paar Instrument Co., Moline, Ill.) equipped with a mixer and heat controller (Model 4843). Aqueous starch suspensions (8%, w/w) were heated at 4° C. $min^{-1}$ and stirred continuously (330 rpm) while heating. Scanning electron micrographs confirm that when starch is heated in water to a temperature of about 95° C., the starch gelatinizes but leaves a starch envelope or remnant that is roughly the size of the original starch granule cf FIG. 1(A). The starch granule remnant limits the particle size that may be obtained. The particle size limitations are overcome by heating the starch melt to at least about over 100° C. and or to at least about 120° C. At 120° C., the starch granule remnants are completely dissolved and the starch the particle size can be reduced to a much smaller diameter cf. FIG. 1.

In this example, a temperature of 120° C. was reached and held for 10 minutes before the melt was cooled to 80° C. and poured into molds. The melt was allowed to gel at 5° C. overnight. The gel was placed into 10 volumes of ethanol (95%) and sheared with a high shear mixer (e.g., an IKA® mixer) to completely disintegrate the gel and disperse it in the ethanol. The ethanol effectively dehydrated the gel and formed white, opaque particles. The particles were filtered and resuspended in 100% ethanol to completely dehydrate the starch particles. The particles were again filtered and spread on trays and dried at 80° C. for two hours. The dried starch particles were placed in a mortar and crushed with a pestle to form a free-flowing, white starch powder.

Example 2

Preparation of Starch Foam Microparticles II

The following example illustrates another exemplary method by which starch foam microparticles are produced.

Temperature treatments were performed as in Example 1. In this example, a temperature of 120° C. was reached and held for 10 min before the melt was pumped through an atomizer. The atomized starch mist was collected in a container of 100% ethanol. The starch particles were filtered and resuspended in 100% ethanol to remove moisture. The starch particles were filtered, dried and ground in a mortar and pestle as in Example 1. The particles that resulted were primarily spherical and formed a free-flowing powder.

Example 3

Plastic Composite Films and Injection Molded Products

The following Example illustrates the use of starch microparticles for the manufacture of plastic composite films and/or injection molded products.

Powders formed as described in Examples 1 and 2 will be gravimetrically fed (K tron Soder Model 9475-70057, Pitman, N.J.) into a Leistritz co-rotating twin-screw (18 mm) extruder (Model MIC 18/GL 30D, Nurnberg, Germany). A second feeder will be used to meter polyethylene pellets into the extruder. The extruder contains six heating zones that will be adjusted to 75/95/115/125/125/100° C. in order from the feed port to the die. The screw speed will be maintained at 60 rpm and the screw configuration will consist of two sections of kneading blocks separated by conveying elements.

The blends will be extruded through a 2 strand (2 mm dia.) rod die and cut into strands approximately 0.5 m in length. The strands will be pelletized (~2.0 mm, micropelletizer, Model 1, Wayne Machine and Die Co., Totowa, N.J.) and used for blowing films or injection molding. The shear within the extruder will effectively disperse the starch microparticles throughout the resin matrix. Starch powders with nanometer particle size ranges will be added up to 50% on a weight basis.

Example 4

Controlling Parsitic Mites in Honeybee Colonies-I

The following Example illustrates the use of starch microparticles for controlling parasitic mites in honeybee colonies.

Powders formed as described in Examples 1 and 2 were prepared. Thymol oil was blended with 100% ethanol (1:3). Eighty grams of starch powder were added to sixty grams of the blend of thymol and ethanol. The starch was air-dried to allow the ethanol to evaporate and simply leave the residual thymol oil. The product was a free-flowing powder with no clumping and containing 20% thymol. This powder was added to other ingredients that were attractive to honeybees. The honeybees readily consumed the starch powder blend. The population of parasitic mites was reduced to 10% of the control.

Example 5

Controlling Varroa Mites in Bee Colonies

The following example illustrates the use of starch foam microparticle encapsulated essential oils for the control of *Varroa* mites in honeybee colonies.

*Varroa destructor*, a parasitic mite of honeybees *Apis mellifera* (L.), has had a catastrophic effect on populations of managed and feral honey bee colonies. Since the economic impact of bees as pollinators and honey producers is large, the health of bee colonies is imperative. Therefore, the use of starch foam microparticle encapsulated essential oils to affect mite control improves bee health and has beneficial economic consequences.

The use of starch foam microparticle encapsulated essential oils is effective for mite control in the contact phase and in the systemic phase.

The "contact phase" is the phase where mites come in contact with the ingested starch encapsulated oils that end up on the exterior of the bee. This occurs much the same way that mites typically pick up cuticular hydrocarbons from the bees on a routine basis. In general, mites have no cuticular hydrocarbons of their own. Thus, the mites pick up oils from the hair and cuticle of bees which under the usual conditions thereby limits their detection in the colony and protects their cuticle. However, without being bound by theory, it is believed that when the bees are treated with the encapsulated oils, the mites pick up a low level of the oils from the bees and this incapacitates the mite.

Figure 3:
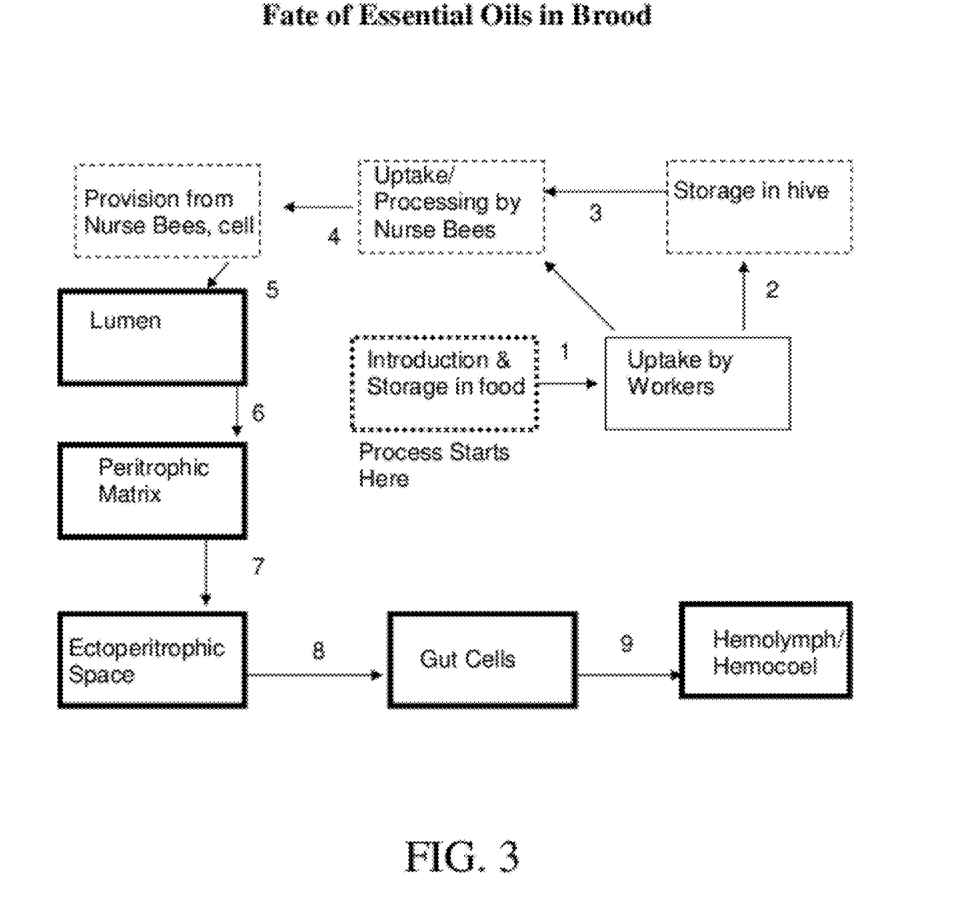
FIG. 3 Shows an exemplary pathway by which oils enter the larval hemolymph.

The "systemic phase" gets oils into the colony through the bees eating the encapsulations and subsequently passing them on to their larvae. FIG. 3 shows the pathway the oils traverse to enter the larval hemolymph (blood).

Experimental

A series of trials were conducted. The trials demonstrated that starch encapsulations, prepared as in Example 4, above, at 25% active ingredient (AI), fed to the bees mixed with powdered sugar at 2.5% final AI effectively controlled mites. Over an eight week period, the starch encapsulated oils significantly reduced mite populations in the treated colonies and reduced mite infestation in brood cells.

Figure 4:
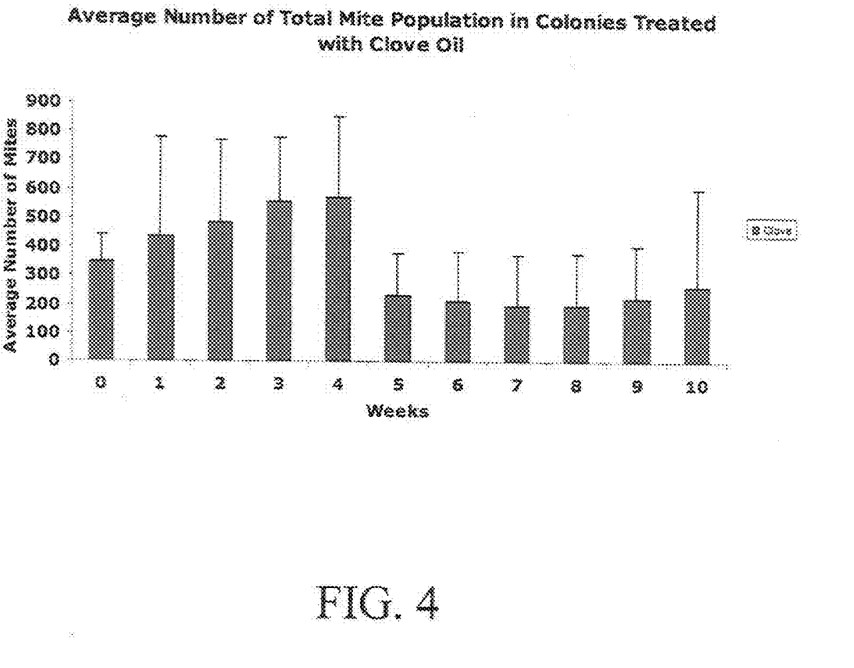
FIG. 4 Shows the number of adult mites found on sticky boards of colonies treated with starch encapsulated clove oil.

FIG. 4 shows the number of adult mites found on sticky boards of colonies treated with starch encapsulated clove oil. Week 1 was a pretreatment time for the quantification of the average number of mites present in the colony. Following week 1, applications of the oils were made as needed in the five treatment nucleus colonies over the experimental period. Fifteen gram treatments were placed on the top bars of the colonies and sticky boards were placed on the bottom boards to catch mites that dropped from the bees. The sticky boards were changed each week.

Mite numbers decreased following the three week incubation time of immature bees. The decrease at week five indicates that there were fewer mites invading cells following the introduction of the oils at week 2. In Week 10, a commercial acaracide (Apistan®) was applied to determine the number of remaining mites that were not affected by the oils. Results of the week 10 Apistan® treatments indicated that there was no difference between previous five weeks and the final application, thereby demonstrating that the treatments were highly effective in reducing mite numbers in the colonies.

Figure 5:
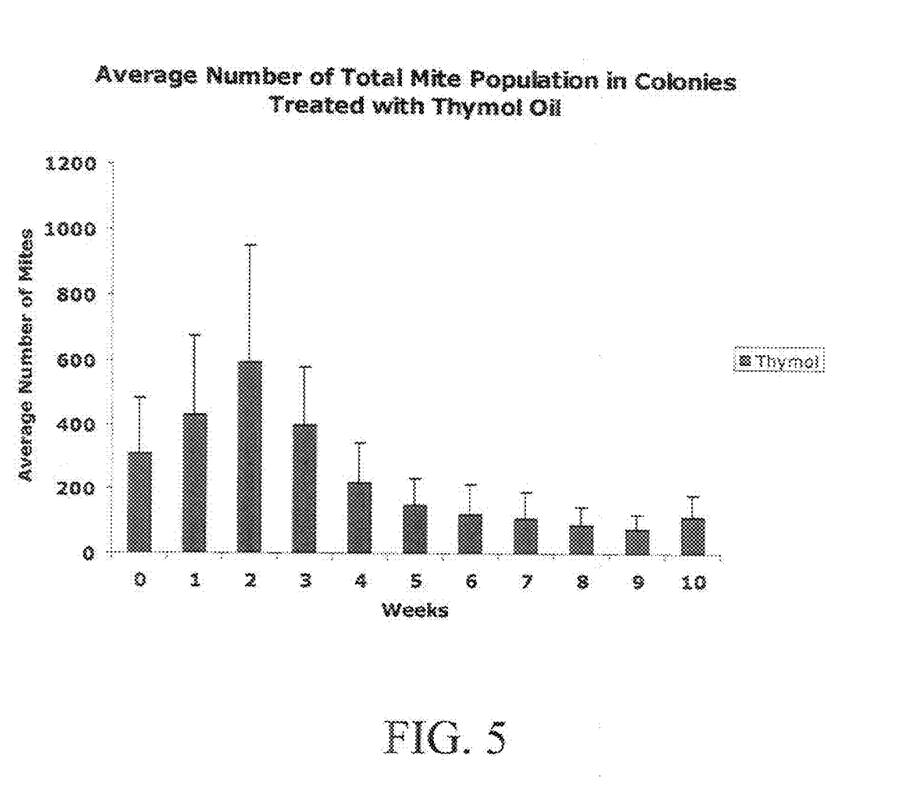
FIG. 5 Shows mite mortality in honey bee colonies treated with starch foam microparticle encapsulated thymol.

In another treatment, shown in FIG. 5, starch encapsulated thymol was applied to five nucleus colonies as described for clove oil treatment above. Results of the thymol treatment were even more dramatic than seen in the clove treatment. Numbers of mites reduced more quickly and were numerically lower in the final weeks of the experiment.

Discussion

Results show that the starch encapsulations are very effective in reducing the number of mites entering cells and are very effective at controlling the number of mites present in the colonies treated with starch foam microparticle encapsulated essential oils. Any effective essential oil can be encapsulated and delivered to colonies using the starch foam microparticle technology. The essential oil can be a single essential oil, or a combination of one essential oil with a carrier oil, or one essential oil combined with one or more other essential oils e.g., thymol; thymol and clove; clove, patchouli, and thymol; etc. . . . .

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A starch foam microparticle wherein:
   (i) the starch foam microparticle has a porous structure, and wherein
   (ii) the starch foam microparticle has a diameter of less than or equal to about 50 microns (μm) at its widest point, and wherein
   (iii). the starch foam microparticle has a density that is in a range that is between about 0.10 g/cm$^3$ and about 1.0 g/cm$^3$.

2. The starch foam microparticle of claim 1, wherein the starch foam microparticle has a density that is in a range that is between about 0.14 g/cm$^3$ and about 0.34 g/cm$^3$.

3. The starch foam microparticle of claim 1, wherein the starch foam microparticle has a density that is less than or equal to about 0.32 g/cm$^3$.

4. The starch foam microparticle of claim 1, wherein the microparticle has a diameter at its widest point that is in a range that is between about 0.1 μm and about 50 μm.

5. The starch foam microparticle of claim 1, wherein the starch foam microparticle has a diameter at its widest point of less than or equal to about 20 μm.

6. The starch foam microparticle of claim 1, wherein the starch foam microparticle comprises a starch that is a plant starch.

7. The starch foam microparticle of claim 6, wherein the starch is a plant starch that is a member selected from the group consisting of a cereal starch, a tuber starch and a legume starch or a combination of such members.

8. The starch foam microparticle of claim 6, wherein the plant starch is member selected from the group consisting of a modified starch and an unmodified starch or a combination of such members.

9. The starch foam microparticle of claim 7, wherein the plant starch is a member selected from the group consisting of corn starch, wheat starch, potato starch, rice starch and high amylose corn starch or a combination of such members.

10. The starch foam microparticle of claim 1, wherein the starch foam microparticle is loaded with a non-aqueous liquid.

11. The starch foam microparticle of claim 10, wherein the non-aqueous liquid comprises at least one oil.

12. The starch foam microparticle of claim 11, wherein the at least one oil is an essential oil.

13. The starch foam microparticle of claim 12, wherein the essential oil has mitocidal properties.

14. The starch foam microparticle of claim 13, wherein the essential oil is member selected from the group consisting of cinnamon oil, thyme oil, clove oil, patchouli oil, wintergreen oil and tea tree oil or a combination of such members.

15. The starch foam microparticle of claim 10, wherein the non-aqueous liquid comprises a pharmaceutical.

16. The starch foam microparticle of claim 10, wherein the non-aqueous liquid comprises a fragrance.

17. The starch foam microparticle of claim 10, wherein the non-aqueous liquid comprises a pheromone.

18. A population of starch foam microparticles wherein the starch foam microparticles comprising the population of starch foam microparticles have a porous structure, have a density that is in a range that is between about 0.14 g/cm$^3$ and about 0.34 g/cm$^3$, and have a diameter that is less than or equal to about 50 μm wherein,
   (i) the population of starch foam microparticles is loaded with a non-aqueous liquid by forming a mixture comprising the non-aqueous liquid and the population of starch foam microparticles, wherein
   (ii) the non-aqueous liquid is present in an amount that is less than or equal to at least about 25% by weight of the mixture, wherein
   (iii) the population of starch foam microparticles absorbs the non-aqueous liquid thereby forming a loaded population of starch foam microparticles, and wherein
   (iv) the loaded population of starch foam microparticles is a free flowing powder.

19. A population of starch foam microparticles wherein the starch foam microparticles comprising the population of starch foam microparticles have a porous structure, have a density that is in a range that is between about 0.14 g/cm$^3$ and about 0.34 g/cm$^3$, and have a diameter that is less than or equal to about 50 μm wherein:
   (i) the starch comprising the population of starch foam microparticles is a an unmodified plant starch that is a member selected from the group consisting of corn starch, high amylose corn starch and wheat starch, or a combination of such members; and
   (ii) the population of starch foam microparticles is loaded with an essential oil that is a member selected from the group consisting of cinnamon oil, thyme oil, clove oil, patchouli oil, wintergreen oil and tea tree oil or a combination of such members.

20. The population of claim 19, wherein the essential oil is present in an amount that is about 25% the weight of the population of starch foam microparticles.

21. A plastic composite film comprising starch foam microparticles wherein the starch foam microparticles:
   (i) have a porous structure; and
   (ii) have a diameter of less than or equal to about 50 μm at their widest point, and wherein
   (iii) the starch foam microparticle has a density that is in a range that is between about 0.10 g/cm$^3$ and about 1.0 g/cm$^3$.

22. The plastic composite film of claim 21, wherein the starch foam microparticles have a density that is in a range that is between about 0.14 g/cm$^3$ and about 0.34 g/cm$^3$.

23. The plastic composite film of claim 21, wherein the starch foam microparticles have a diameter at their widest point that is less than or equal to about 25% of the film thickness.

24. The plastic composite film of claim 21, wherein the starch foam microparticles have a diameter at their widest point that is in a size rage that is between about 0.1 μm and about 5 μm.

25. The plastic composite film of claim 24, wherein the starch foam microparticles:
   (i) have a diameter at their widest point that is in a range that is between about 100 nm and about 999 nm, and
   (ii) are present on a weight basis in the plastic composite film in an amount that is less than or equal to about 50%.

* * * * *